United States Patent [19]

Kiegel et al.

[11] Patent Number: 5,734,042
[45] Date of Patent: Mar. 31, 1998

[54] PROCESS FOR THE PRODUCTION OF ASYMMETRICAL PHOSPHORIC ACID DIESTERS

[75] Inventors: Einhard Kiegel; Harald Zilch, both of Mannheim, Germany

[73] Assignee: Boehringer Mannheim GmbH, Mannheim, Germany

[21] Appl. No.: 682,571

[22] PCT Filed: Jan. 21, 1995

[86] PCT No.: PCT/EP95/00219

§ 371 Date: Jul. 29, 1996

§ 102(e) Date: Jul. 29, 1996

[87] PCT Pub. No.: WO95/20596

PCT Pub. Date: Aug. 3, 1995

[30] Foreign Application Priority Data

Jan. 28, 1994 [DE] Germany .................. 44 02 492.4

[51] Int. Cl.$^6$ .................. C07H 1/02; C07H 19/10; C07H 19/207; C07F 9/09
[52] U.S. Cl. .................. 536/26.71; 536/26.72; 536/26.8; 558/118; 558/119
[58] Field of Search .................. 536/26.71, 26.72, 536/26.8; 558/118, 119

[56] References Cited

U.S. PATENT DOCUMENTS

| | | | |
|---|---|---|---|
| 4,239,905 | 12/1980 | Kodama et al. | 536/26.8 |
| 4,605,645 | 8/1986 | Watanabe et al. | 536/26.8 X |

*Primary Examiner*—Michael G. Ambrose
*Attorney, Agent, or Firm*—Nikaido Marmelstein Murray & Oram LLP

[57] ABSTRACT

The present invention concerns a process for the production of asymmetrical phosphoric acid diesters.

The process is characterized in that a phosphoric acid ester is condensed with a compound containing hydroxy groups in the presence of an arylsulfonic acid chloride and an organic base, the residue of evaporation is stirred out with an organic solvent after the hydrolysis, the arylsulfonic acid pyridine salt which forms is nearly completely crystallized and recycled, the lipid derivative that is formed is precipitated as a sparingly soluble salt by addition of a solution containing alkaline-earth ions and isolated, the sparingly soluble salt is isolated as the free acid in an organic solvent by suspension in a water-immiscible organic solvent and a dilute aqueous mineral acid, the crude product is purified if desired, by means of preparative chromatography on a RP phase and subsequently the free acid is converted if desired into any desired salt.

16 Claims, No Drawings

PROCESS FOR THE PRODUCTION OF ASYMMETRICAL PHOSPHORIC ACID DIESTERS

This application is a 371 of PCT/EP95/00219 filed Jan. 21, 1995.

The present invention concerns a process for the production of phosphoric acid diesters with two non-identical organic residues.

The process according to the invention for the production of phosphoric acid diesters is characterized in that

[a] a phosphoric acid ester of formula I,

$$R^1\text{—O—P(O)(OH)}_2 \quad (I)$$

in which $R^1$ represents an organic residue, is condensed with an alcohol of formula II

$$R^2\text{—OH} \quad (II)$$

in which $R^2$ represents an organic residue,
in the presence of an arylsulfonic acid chloride and an organic phase, (b) the phosphoric acid diester which is formed is precipitated as a sparingly soluble salt by the addition of a solution containing alkaline-earth ions and it is isolated, (c) the sparingly soluble salt is isolated as the free acid in an organic solvent by suspension in a water-immiscible organic solvent and a dilute aqueous mineral acid.

The product that is formed is subsequently purified further. This can for example be achieved by purifying the crude product obtained after step [c] by preparative chromatography on an appropriate column, for example a reversed phase column (RP=reversed phase) (step [d]) and if desired the compound obtained in the form of its free acid is subsequently converted into any desired salt (step [e]).

In certain cases in which the alcohol of formula II has for example further secondary OH groups in addition to a primary OH group, it may be advantageous to react the phosphoric acid ester of formula I with the arylsulfonic acid chloride in the presence of an organic base (producing the mixed anhydride) and only afterwards add the alcohol of formula II.

The process claimed is particularly suitable for the production of liponucleotides in which $R^2$ represents a nucleosidic residue.

Three different processes for the production of lipid derivatives of nucleosides are shown in WO 92/03462:
1. Reaction of a lipid phosphate dichloride with the nucleoside in the presence of an organic base.
2. Enzymatic catalysis of the reaction of a lipid phosphoric acid monocholine ester with the nucleoside (phospholipase D from Streptomyces).
3. Condensation of the lipid phosphate with the nucleoside in the presence of DCC (dicyclohexylcarbodiimide).

All three variants are suitable for making internucleotidic bonds as well as for condensing nucleosides with lipid phosphates and are described in the literature.

The condensation of a lipid phosphate and of a nucleoside using DCC is described in J. Med. Chem. 34, 1408 (1991), Biochem. Biophys. Res. Commun. 171, 451 (1990) and U.S. Pat. No. 5,149,794. The enzymatically catalyzed condensation of a phosphocholine with a nucleoside in the presence of phospholipase D from Streptomyces is described in Biochem. 31, 4757 (1992). EP 0 457 570, EP 0 262 876 and WO 92/17487. In addition the use of arylsulfonic acid chlorides for the synthesis of the internucleotidic bonds has been propagated by Khorana et al., in various publications [e.g. J. Am. Chem. Soc. 88, 829 (1966), dto. 86, 1630 (1964)] and especially the sterically hindered 2,4,6-triisopropylbenzenesulfonic acid chloride. This reagent was used by Hostetler et.al. for the condensation of phospholipids with nucleosides and is described inter alia in J. Biol. Chem. 265, 6112 (1990), dto. 266, 11714 (1991). Analogously it was possible to condense nucleoside monophosphates with primary lipid alcohols as described in J. Biol. Chem. 267, 20288 (1992).

However, the described methods have the disadvantage that the production of lipid derivatives is only possible in unsatisfactory yields. Further disadvantages are in addition inadequate product purities and complicated purification procedures which impede mechanization on a large technical scale of for example amounts of several kilograms. It was not even possible to reproduce the published processes in the described yields with larger process batches.

It was possible to eliminate these difficulties with the process according to the invention.

A particular subject matter of the present invention is a process for the production of lipid derivatives which is characterized in that

[a] a phosphoric acid ester of formula I in which $R^1$ represents an organic residue, such as e.g. a special lipid moiety, is condensed with a 5' unprotected nucleoside in the presence of an arylsulfonic acid chloride and an organic base such as e.g. pyridine,

[b] after hydrolysis, the residue of evaporation is stirred out with an organic solvent (e.g. DIPE, MTB), the arylsulfonic acid pyridine salt which is formed is almost completely crystallized and recycled,

[c] the liponucleotide is precipitated as a sparingly soluble salt by addition of e.g. aqueous calcium acetate solution and isolated,

[d] the sparingly soluble salt is isolated as a free acid in an organic solvent by suspension in a water-immiscible organic solvent and a dilute aqueous mineral acid (residue of evaporation >95% area after HPLC).

The crude product is subsequently purified by preparative chromatography on a RP phase and the free acid is converted into any desired salt.

If desired an intermediate isolation is possible after HPLC from the fractions containing product by precipitation of the calcium salt and subsequent conversion into the free acid and into the sodium salt (as described above).

It is only this special combination of various process steps which represents a decisive improvement that enables the production of appropriate compounds in an economic manner on a multi-kg scale.

The condensation in the presence of an arylsulfonic acid chloride is also possible when using a nucleoside monophosphate and a lipid alcohol in which case the subsequent process steps are identical.

The lipid phosphate that is used can be added as a crude product without having a significant influence on the product purity or the yield relative to the nucleoside.

A suitable base is for example pyridine or lutidine in an inert organic solvent such as toluene or the reaction is carried out directly in the base without a further solvent.

Benzene-, toluene-, 2,4,6-trimethylbenzene-, 2,6-dimethylbenzene-, 2,4,6-triisopropylbenzene- or 2,6-diisopropylbenzene-sulfonic acid come into consideration as arylsulfonic acid chlorides. The more bulky the substituents in the ortho positions are, the less by-products are to be expected.

In some cases a sterically hindered carboxylic acid chloride or a phosphoric acid chloride can be used instead of the arylsulfonic acid chloride.

Pivaloyl chloride is mentioned as an example of a carboxylic acid chloride that can be used. A compound of formula III which formally represents an anhydride of the phosphate of formula I is also to be understood as an active intermediate step for the condensation with the nucleoside when using a phosphoric acid chloride.

Calcium in the form of its acetate, hydroxide, carbonate or hydride is preferably used to precipitate the sparingly soluble salt due to its good physiological compatability and the poor solubility of its salts in organic solvents.

The chromatographic purification is preferably carried out on a reversed phase using a methanol/buffer solution as the eluant. In the final stage the isolated free acid is converted into a physiologically tolerated salt e.g. a potassium, lithium or sodium salt.

within the meaning of the present invention $R^1$ is preferably a lipid residue of the general formula IV

in which A and B can be the same or different and denote hydrogen, $C_1$–$C_{18}$ alkyl, $C_1$–$C_{18}$ alkoxy, $C_1$–$C_{18}$ alkylthio, $C_1$–$C_{18}$ alkylsulfinyl or $C_1$–$C_{18}$ alkylsulfonyl or $R^1$ is a straight-chained or branched, saturated or unsaturated alkyl chain with 10–20 carbon atoms which can, if desired, be substituted once or several times by halogen, $C_1$–$C_6$ alkoxy, $C_1$–$C_6$ alkylmercapto.

$R^2$ preferably represents a 5' nucleoside residue of the general formula V

in which $R^3$ denotes hydrogen, halogen or a hydroxy group, $R^4$, $R^5$ each denote hydrogen or one of the residues $R^4$ and $R^5$ denotes halogen, a hydroxy, a cyano, an amino or an azido group and $R^3$ and $R^4$ in addition can represent a further bond between C-2' and C-3', $R^{5'}$ denotes hydrogen, hydroxy, azide, amino, cyano or halogen or it represents a seco-nucleoside residue of the general formula V a

in which

R represents a hydrogen atom or a $C_1$–$C_3$ alkyl group which is substituted if desired by hydroxy, halogen or azide and B denotes one of the following compounds:

1.)

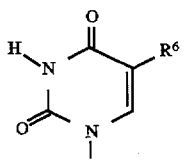

in which $R^6$ can be hydrogen, an alkyl chain with 1–4 carbon atoms which can be substituted by halogen, an alkenyl or alkinyl residue with 2–6 carbon atoms which can be substituted if desired by halogen or it can be halogen

2.)

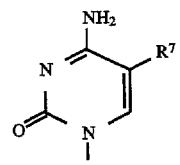

in which $R^7$ can be hydrogen, an alkyl chain with 1–4 carbon atoms which can be substituted by halogen or it can be halogen

3.)

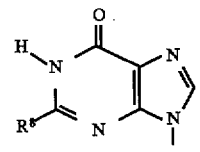

in which $R^8$ can be hydrogen, an alkyl chain with 1–4 carbon atoms, halogen or a hydroxy or amino group

4.)

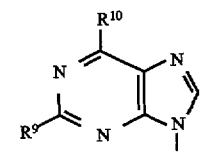

in which $R^9$ can be hydrogen, halogen or an amino group and $R^{10}$ denotes hydrogen, halogen, mercapto, $C_1$–$C_6$ alkoxy, $C_1$–$C_6$ alkylmercapto or an amino group which can be mono- or disubstituted by $C_1$–$C_6$ alkyl, $C_1$–$C_6$ alkoxy, hydroxy, $C_2$–$C_6$ alkyl and/or $C_3$–$C_6$ cycloalkyl, aryl, hetaryl, aralkyl or hetarylalkyl groups which can be further substituted if desired in the aryl or hetaryl residue by one or several hydroxy, methoxy or alkyl groups or by halogen or it denotes allyl which can be substituted if desired by monoalkyl or dialkyl or alkoxy groups.

$R^2$ preferably denotes a residue selected for example from the group:

-2',3'-dideoxy-3'-azidouridine
-2',3'-dideoxyinosine
-2',3'-dideoxyguanosine
-2',3'-dideoxycytidine
-2',3'-dideoxyadenosine
-3'-deoxythymidine
-2',3'-dideoxy-2',3'-didehydro-$N^6$-(0-methylbenzyl)-adenosine
-2',3'-dideoxy-2',3'-didehydro-$N^6$-(2-methylpropyl)-adenosine
-2',3'-dideoxy-3'-azidoguanosine
-3'-deoxy-3'-azidothymidine
-2',3'-dideoxy-3'-fluoro-5-chlorouridine
-2',3'-deoxy-3'-fluorothymidine
-2',3'-dideoxy-3'-fluoroadenosine
-2',3'-dideoxy-3'-fluoro-2,6-diaminopurine riboside
-2',3'-dideoxy-2',3'-didehydrocytidine
-3'-deoxy-2',3'-didehydrothymidine
-3'-deoxy-3'-azidothymidine
-5-fluorouridine
-5-trifluoromethyl-2'-deoxyuridine
-6-mercaptopurine-9-β-D-ribofuranoside
-2-fluoroadenine-9-β-D-arabinofuranoside
-2-chloro-2'-deoxyadenosine
-Acylclovir
-Ganciclovir

EXAMPLE 1

Production of the crude product of (3'-deoxy-3'-azidothymidine)-5'-phosphoric acid-(3-dodecylthio-2-decyloxy)propyl ester 509 g (0.95 mol) 3-dodecylthio-2-decyloxy-propanol-1-monophosphate are dissolved at room temperature in 2.84 l dry pyridine. 443.8 g (1.467 mol) triisopropylbenzene-sulfonic chloride is added to the solution, followed by 229 g (0.857 mol) AZT; it has all dissolved after stirring for ca. 10 min at room temperature. The brown solution is stirred overnight at room temperature. Then 1.43 l water is added and it is stirred for a further 30 minutes at room temperature; the mixture becomes turbid on addition of water but becomes clear again when restirred. The solution is concentrated by evaporation at ca. 60° C. bath temperature in a vacuum using a rotary evaporator and the evaporation residue is twice redistilled with 2.8 l toluene each time to remove pyridine. 5.7 l diisopropyl ether is poured over the semi-solid evaporation residue and it is stirred for ca. 1 hour in an ice bath. The salt is suction filtered (pyridine salt of triisopropylbenzenesulfonic acid) and it is rewashed in portions with 700 ml diisopropyl ether. The salt is dried at 50° C. (615 g) and stored or recycled. The ether filtrate is shaken three times with 1.8 l 2 n HCl in each case. If a good phase separation is not achieved, then the emulsion layer is carefully suction filtered over a Fibrazell layer. The organic phase is dried with sodium sulfate and concentrated to a constant weight by evaporation.

Measured weight 677 g crude phosphoric acid diester ("106%" of theory in relation to AZT) HPLC: ca. 76 area % (percentage area).

EXAMPLE 2

Purification of the crude phosphoric acid diester by Ca salt formation 283 g (0.38 mol) of the crude product from example 1 is dissolved at room temperature in 1.73 l methanol and 850 ml water while stirring. A solution of 60.1 g Ca-acetate hydrate in 400 ml water is added dropwise at room temperature within ca. 45 minutes; a greasy precipitate is firstly formed which is restirred for a longer period (e.g. overnight). In this process the precipitate becomes powdery. The calcium salt is suction filtered and, while wet from the nutsch, it is intensively stirred out for ca. 30 minutes at room temperature with 1 l acetone. It is filtered by suction and dried. Measured weight 192 g.

The calcium salt is suspended in 1.2 l methyl-tert.butyl ether and 276 ml 2 n HCl and stirred intensively until the salt has disintegrated and a slightly turbid water phase has formed. After separating the phases, the MTB phase is washed twice with 250 ml saturated NaCl solution each time, dried over $Na_2SO_4$ and concentrated by evaporation.

Residue of evaporation: 179.1 g (63.2 % of the amount used) HPLC 90.46 area %

EXAMPLE 3

Purification of the crude product by preparative HPLC
Preparative system:
stationary phase: Merck LiChroprep RP 18; 15–25 μ
mobile phase: 0.02 molar $NaH_2PO_4$ solution 12.5%+ methanol 87.5%

125 g of the crude product from example 2 is dissolved in 750 ml methanol at ca. 35° C. 1.5 l mobile phase is added and it is adjusted to pH 5 with concentrated NaOH. The solution is filtered and the filtrate is filled up to 2.5 l with mobile phase. This solution is chromatographed in portions of 500 ml.

It is fractionated from the maximum of the main peak and a fraction of 1.2 l is cut. The combined pure fractions from 5 separations (6 l) are concentrated on a rotary evaporator at 40° C. bath temperature in a vacuum to form a viscous residue. The residue is rinsed in portions with a total of 500 ml water from the apparatus and adjusted to pH 2 with semi-concentrated HCl.

It is extracted with methyl-tert.butyl ether (1×2 l; 2×1 l); the phases separate almost cleanly and may be slightly turbid. In the 3rd extraction both phases are usually clear.

The combined MTB extracts are shaken twice with 250 ml saturated NaCl solution each time in order to remove water. The organic phase is dried over $Na_2SO_4$ and concentrated by evaporation to a constant weight. Measured weight: ca. 70 g HPLC: ca. 99.5 area %.

EXAMPLE 4

Production of the Na salt 278.3 g (0.327 mol) of the HPLC-purified product from example 3 is dissolved in 4.8 l methanol at room temperature; 760 ml water is added to the solution (it becomes milky). It is adjusted against a calibrated electrode to pH 5.8 with 1 n NaOH (ca. 300 ml) and the turbid solution is sucked over a Seitz filter plate. The clear filtrate is concentrated on a rotary evaporator in a vacuum. The residue of evaporation is redistilled four times with toluene. 5.8 l acetone is poured over the dry residue of evaporation and it is stirred for ca. 1 h at room temperature. It is suction filtered, washed with a small amount of acetone and dried at ca. 50° C.

Yield: 278 g (97% of theory in relation to the purified free acid) HPLC: 99.45 area-%.

EXAMPLE 5

Production of sodium salt by precipitation from a toluene solution 3 g (0.0978 mol) purified free acid from example 3 is dissolved in 500 ml toluene. The slightly turbid solution is filtered over a Seitz filter. The required amount for the salt formation (which is previously determined on an aliquot) of a 30% sodium methylate solution is added to the toluene solution while stirring. The clear, slightly yellow solution is slowly added dropwise to 3 l acetone while stirring. It is stirred further, overnight if necessary, until the precipitate becomes powdery. The precipitate is suction filtered; the nutsch may become sticky towards the end of the suction. It is rinsed with a small amount of acetone and the slightly sticky product is dried at 50° C.

Yield 66.2 g (88.1% of theory).

EXAMPLE 6

Production of (3'-deoxy-3'-azido-thymidine)-5'-phosphoric acid (3-dodecylthio-2-decyloxy)-propyl ester using benzenesulfonyl chloride 17.3 g (0.034 mol) 3-dodecylthio-2-decyloxy-propanol-1-monophosphate is dissolved in 100 ml absolute pyridine analogously to example 1, it is admixed with 6.5 ml (0.051 mol) benzenesulfonyl chloride and stirred for a further 4 hours at room temperature. 8 g (0.03 mol) AZT is then added and it is processed further analogously to example 1. The crude product (24.5 g; "109%" of theory relative to AZT) is converted analogously to examples 3 to 5 into the sodium salt. Yield 12.2 g (52.9 % of theory relative to AZT) HPLC: 99.43 area %.

EXAMPLE 7

Production of the Ca salt of (3'-deoxy-3'-azido-thymidine)-5'-phosphoric acid-(3-dodecylthio-2-decyloxy)propyl ester using 2,4,6-trimethylbenzenesulfonyl chloride 86.8 g (0.17 mol) 3-dodecylthio-2-decyloxy-propanol-1-monophosphate is allowed to react with 57.7 g (0.26 mol) 2,4,6-trimethylbenzenesulfonyl chloride in 515 ml absolute pyridine analogously to example 6 and then reacted with 41.2 g (0.154 mol) AZT according to example 1. The crude product obtained analogously to example 1 (138 g; "119" % of theory relative to AZT) is converted into the crude Ca salt analogously to example 2. Yield 98.2 g (83.2% of theory relative to AZT).

EXAMPLE 8

Production of (3'-deoxy-3'-fluorothymidine)-5'-phosphoric acid-(3-dodecylthio-2-decyloxy)propyl ester sodium salt 78.9 g (0.159 mol) 3-dodecylthio-2-decyloxypropanol-1-monophosphate in 480 ml absolute pyridine is reacted with 35 g (0.143 mol) 3'-deoxy-3'-fluorothymidine (FLT) in the presence of 72.55 g (0.239 mol) 2,4,6-triisopropylbenzenesulfonyl chloride analogously to example 1. Measured weight 136 g crude product (130% in relation to FLT). The crude product is precipitated as a calcium salt analogously to example 2, the precipitate is converted into the free acid and purified by preparative column chromatography on a RP-18 analogously to example 3 and converted into the sodium salt analogously to examples 4+5. Yield 74 g (69% of theory relative to FLT), HPLC: 99.41 area %.

EXAMPLE 9

Production of (2,3'-dideoxy-inosine)-5'-phosphoric acid (3-dodecylthio-2-decyloxy)propyl ester sodium salt 15.8 g (32 mmol) 3-dodecylthio-2-decyloxy-propanol-1-monophosphate in 100 ml absolute pyridine is admixed with 14.5 g (48 mmol) 2,4,6-triisopropylbenzenesulfonyl chloride analogously to example 6 and after 4 hours it is reacted with 6.77 g (29 mmol) 2',3'-dideoxyinosine (DDI). The crude product is converted into the sodium salt analogously to examples 3 to 5. Yield 13.04 g (61% of theory relative to DDI), HPLC: 99.4 area %.

EXAMPLE 10

Production of (3'-deoxy-3'-azidothymidine)-5'-phosphoric acid-[2,3-bis(undecyloxy)]propyl ester sodium salt 15.8 g (32 mmol) 2,3 bis-(undecyloxy)propanol-1-monophosphate is dissolved in 96 ml absolute pyridine analogously to example 1 and reacted with 6.77 g (29 mmol) 3'-azido-3'-deoxythymidine (AZT) in the presence of 14.5 g (48 mmol) 2,4,6-triisopropylbenzenesulfonyl chloride. The crude product is converted into the sodium salt analogously to examples 3 to 5. Yield 17.15 g (77% of theory relative to AZT), HPLC: 99.7 area %.

EXAMPLE 11

The following compounds were prepared analogously to example 1 as a crude product, isolated by means of the calcium salt analogously to example 2, purified by means of preparative HPLC analogously to example 3 and converted into the sodium salt analogously to example 5:

1. (3'-Deoxy-3'-azidothymidine)-5'-phosphoric acid-(3-undecylmercapto-2-undecyloxy)propyl ester sodium salt melting point 218°–222° C. decomp., $R_f$=0.55 (mobile solvent: isopropanol/butyl acetate/water=5/3/2)

2. (3'-Deoxy-3'-azidothymidine)-5'-phosphoric acid-(3-dodecyloxy-2-decyloxy)propyl ester sodium salt melting point 205°–211° C. decomp., $R_f$=0.60 (mobile solvent: isopropanol/butyl acetate/water=5/3/2)

3. (3'-Deoxy-3'-azidothymidine)-5'-phosphoric acid-(3-decylmercapto-2-dodecyloxy)propyl ester sodium salt melting point >206° C. decomp., $R_f$=0.24 (mobile solvent: MeOH/$H_2O$=8/2)

4. (3'-Deoxy-3'-azidothymidine)-5'-phosphoric acid-(3-decylmercapto-2-decyloxy)propyl ester sodium salt melting point >207° C. decomp., $R_f$=0.45 (mobile solvent: isopropanol/butyl acetate/water=5/3/2)

5. (3'-Deoxy-3'-azidothymidine)-5'-phosphoric acid-hexadecyl ester sodium salt melting point 227°–230° C. decomp., $R_f$=0.55 (mobile solvent: isopropanol/butyl acetate/water=5/3/2)

6. (3'-Deoxy-3'-azidothymidine)-5'-phosphoric acid-(3-tetradecylmercapto-2-decyloxy)propyl ester sodium salt melting point 155° C., $R_f$=0.30 (mobile solvent: ethyl acetate/methanol=3/1)

7. (3'-Deoxy-3'-azidothymidine)-5'-phosphoric acid-(3-dodecylmercapto)propyl ester sodium salt melting point >200° C. decomp., $R_f$=0.20 (mobile solvent: ethyl acetate/methanol=3/1)

8. (3'-Deoxy-3'-azidothymidine)-5'-phosphoric acid-(3-dodecylmercapto-2-dodecyloxy)propyl ester sodium salt melting point >170° C. decomp., $R_f$=0.25 (mobile solvent: ethyl acetate/methanol=3/1)

9. (3'-Deoxy-3'-azidothymidine)-5'-phosphoric acid-(3-decylmercapto-2-hexadecyloxy)propyl ester sodium salt melting point 135° C., $R_f$=0.35 (mobile solvent: ethyl acetate/methanol=3/1)

10. (3'-Deoxy-3'-azidothymidine)-5'-phosphoric acid-(2-dodecyloxy)tetradecyl ester sodium salt melting point 83° C., $R_f$=0.35 (mobile solvent: ethyl acetate/methanol=3/1)

11. (3'-Deoxy-3'-azidothymidine)-5'-phosphoric acid-(3-tridecylmercapto-2-decyloxy)propyl ester sodium salt melting point >190° C. decomp., $R_f$=0.20 (mobile solvent: ethyl acetate/methanol=3/1)

12. (3'-Deoxy-3'-azidothymidine)-5'-phosphoric acid-(3-dodecylmercapto-2-octyloxy)propyl ester sodium salt melting point >200° C. decomp., $R_f$=0.60 (mobile solvent: methylene chloride/methanol/water=65/25/4)*

13. (3'-Deoxy-3'-azidothymidine)-5'-phosphoric acid-(3-undecylmercapto-2-decyloxy)propyl ester sodium salt melting point >200° C. decomp., $R_f$=0.25 (mobile solvent: ethyl acetate/methanol=3/1)

14. (3'-Deoxythymidine)-5'-phosphoric acid-(3-dodecylmercapto-2-decyloxy)propyl ester sodium salt 15. Thymidine-5'-phosphoric acid-(3-dodecylmercapto-2-decyloxy)propyl ester sodium salt melting point 251°–254° C. decomp., $R_f$=0.45 (mobile solvent: n-propanol/H$_2$O=9/1)
16. (6-Mercaptopurine-9-β-D-ribofuranoside)-5'-phosphoric acid-(3-dodecylmercapto-2-decyloxy)-propyl ester sodium salt melting point >200° C. decomp., $R_f$=0.45 (mobile solvent: isopropanol/butyl acetate/conc. ammonia/water=50/30/5/15)
17. (5-Fluorouridine)-5'-phosphoric acid-(3-dodecylmercapto-2-decyloxy)propyl ester sodium salt melting point >210° C. decomp., $R_f$=0.55 (mobile solvent: methylene chloride/methanol/water=65/25/4)
18. (2',3'-Dideoxycytidine)-5'-phosphoric acid-(3-dodecylmercapto-2-decyloxy)-propyl ester sodium salt melting point 202°–205° C. decomp., $R_f$=0.50 (mobile solvent: isopropanol/butyl acetate/water=5/3/2)
19. (3-Deoxy-3'-fluorothymidine)-5'-phosphoric acid-(3-undecylmercapto-2-undecyloxy)-propyl ester sodium salt melting point >200° C. decomp., $R_f$=0.15 (mobile solvent: CH$_2$Cl$_2$/MeOH=8/2)
20. (6-Methylmercaptopurine-9-β-D-ribofuranoside)-5'-phosphoric acid-(3-dodecylmercapto-2-decyloxy)propyl ester sodium salt melting point >170° C. decomp., $R_f$=0.22 (mobile solvent: isopropanol/butyl acetate/water/conc. ammonia 50/30/15/5)
21. 2'-(9-{[(1-Hydroxymethyl)ethoxy]methyl}guanine) phosphoric acid-(3-dodecylmercapto-2-decyloxy)-propyl ester sodium salt $R_f$=0.73 (mobile solvent: H$_2$O/MeOH 0.5/9.5 on RP-8), $R_f$=0.30 (mobile solvent: CH$_2$Cl$_2$/MeOH/H$_2$O 6.5/2.5/0.4 on silica gel)
22. 2'-[9-(Ethoxymethyl)guanine]-phosphoric acid-(3-dodecylmercapto-2-decyloxy)propyl ester sodium salt $R_f$=0.77 (mobile solvent: H$_2$O/MeOH 0.5/9.5 on RP-8), $R_f$=0.35 (CH$_2$Cl$_2$/MeOH/H$_2$O 6.5/2.5/0.4 on silica gel)

We claim:

1. A process for producing an asymmetrical phosphoric acid diester, comprising:
   (a) condensing a phosphoric acid ester of formula I, $$R^1\text{—O—P(O)(OH)}_2 \qquad (I)$$

wherein $R^1$ is a lipid residue of formula IV

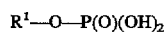

$$\begin{array}{l} \text{CH}_2\text{—A} \\ | \\ \text{CH—B} \\ | \\ \text{CH}_2\text{—} \end{array} \qquad (IV)$$

wherein A and B are the same or different, and each is selected from the group consisting of hydrogen, $C_1$–$C_{18}$ alkyl, $C_1$–$C_{18}$ alkoxy, $C_1$–$C_{18}$ alkylthio, $C_1$–$C_{18}$ alkylsulfinyl and $C_1$–$C_{18}$ alkylsulfonyl, or
   $R^1$ is a straight-chained or branched, saturated or unsaturated alkyl chain with 10–20 carbon atoms which is unsubstituted or substituted at least once by a substituent selected from the group consisting of halogen, $C_1$–$C_6$ alkoxy and $C_1$–$C_6$ alkylmercapto,
   with an alcohol of formula II $$R^2\text{—OH} \qquad (II)$$

wherein $R^2$ represents an organic residue,
   in the presence of (1) an acid chloride selected from the group consisting of aryl sulfonic acid chloride, sterically hindered carboxylic acid chloride and phosphoric acid chloride and (2) an organic base, to form a reaction mixture containing a phosphoric acid diester,
   (b) precipitating the phosphoric acid diester formed in step (a) to produce a sparingly soluble salt by combining a solution containing alkaline-earth ions with the reaction mixture, and
   (c) isolating the sparingly soluble salt formed in step (b) to produce a free acid.

2. The process of claim 1, wherein the sparingly soluble salt is isolated by suspending the sparingly soluble sale in a water-immiscible organic solvent and a dilute aqueous mineral acid.

3. The process of claim 1, further comprising the steps of:
   (d) after step (c), purifying the free acid to produce a purified product, and
   (e) after step (d), converting the purified product into a physiologically tolerated salt.

4. The process of claim 3, wherein in step (d), the free acid is purified by preparative chromatography.

5. The process of claim 1, wherein $R^2$ is a nucleosidic residue.

6. The process of claim 5, wherein $R^2$ is a 5' unprotected nucleoside.

7. The process of claim 1, wherein the organic base is pyridine or lutidine.

8. The process of claim 1, wherein the phosphoric acid ester is condensed with the alcohol in the presence of an aryl sulfonic acid chloride and an organic base.

9. The process of claim 8, wherein the aryl sulfonic acid chloride is selected from the group consisting of benzenesulfonic acid chloride, toluene-sulfonic acid chloride, 2,4,6-trimethylbenzene-sulfonic acid chloride, 2,6-dimethylbenzene-sulfonic acid chloride, 2,4,6-triisopropylbenzene-sulfonic acid chloride, and 2,6-diisopropylbenzene-sulfonic acid chloride.

10. The process of claim 1, wherein the sterically hindered carboxylic acid is pivaloyl chloride.

11. The process of claim 1, wherein the solution containing alkaline-earth lens comprises calcium as the alkaline-earth ion.

12. The process of claim 4, wherein in step (d), the crude product is purified by reverse phase chromatography using a methanol/buffer solution as an eluant.

13. The process of claim 1, wherein $R^2$ is a 5' nucleoside residue of formula V

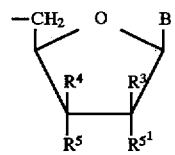

$$\begin{array}{c} \text{—CH}_2 \quad O \quad B \\ \diagdown \diagup \\ R^4 \quad R^3 \\ | \quad | \\ R^5 \quad R^{5'} \end{array} \qquad (V)$$

wherein:
   $R^3$ is selected from the group consisting of hydrogen, halogen and a hydroxy group,
   one of $R^4$ and $R^5$ is hydrogen, and the other of $R^4$ and $R^5$ is selected from the group consisting of hydrogen, halogen, hydroxy, cyano, amino and azido, or
   $R^3$ and $R^4$ are a further bond between C-2' and C-3',
   $R^5$ is selected from the group consisting of hydrogen, hydroxy, azido, amino, cyano, halogen and a seconucleoside residue of formula Va

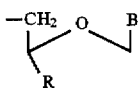

(Va)

wherein
R is a hydrogen atom or a $C_1$–$C_3$ alkyl group which is unsubstituted or has a substituent selected from the group consisting of hydroxy, halogen and azido, and
B is selected from the group consisting of:

1.)

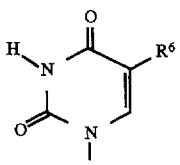

wherein
$R^6$ is selected from the group consisting of hydrogen, halogen and an alkyl chain of 1–4 carbon atoms which is unsubstituted or has a substituent selected from the group consisting of halogen, an alkenyl with 2–6 carbon atoms and an alkynyl with 2–6 carbon atoms, which alkenyl or alkynyl substituent is unsubstituted or substituted by halogen,

2.)

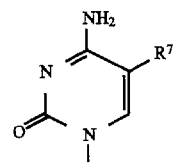

wherein
$R^7$ is selected from the group consisting of hydrogen, halogen and an alkyl chain of 1–4 carbon atoms, which chain is unsubstituted or substituted by halogen,

3.)

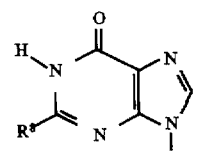

wherein
$R^8$ is selected from the group consisting of hydrogen, an alkyl chain with 1–4 carbon atoms, halogen, hydroxy and amino,

4.)

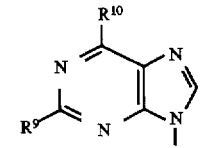

wherein
$R^9$ is selected from the group consisting of hydrogen, halogen and amino and
$R^{10}$ is selected from the group consisting of hydrogen, halogen, mercapto, $C_1$–$C_6$ alkoxy, $C_1$–$C_6$ alkylmercapto and unsubstituted or substituted amino, which substituted amino is mono- or di-substituted by a substituent selected from the group consisting of $C_1$–$C_6$ alkyl, $C_1$–$C_6$ alkoxy, hydroxy, $C_2$–$C_6$ alkyl, $C_3$–$C_6$ cycloalkyl, aryl, hetaryl, aralkyl and hetarylalkyl which aryl, hetaryl, aralkyl or hetarylalkyl substituents are unsubstituted or substituted at least once in the aryl or hetaryl residue thereof by a substituent selected from the group consisting of hydroxy, methoxy, alkyl and halogen, or
$R^{10}$ is allyl which is unsubstituted or substituted by mono- or di-alkyl or alkoxy.

14. The process of claim 1, wherein $R^2$ is selected from the group consisting of:

2',3'-dideoxy-3'-azidouridine
2',3'-dideoxyinosine
2',3'-dideoxyguanosine
2',3'-dideoxycytidine
2',3'-dideoxyadenosine
3'-deoxythymidine
2',3'-dideoxy-2',3'-didehydro-$N^6$-(0-methylbenzyl)-adenosine
2',3'-dideoxy-2',3'-didehydro-$N^6$-(2-methylpropyl)-adenosine
2',3'-dideoxy-3'azidoguanosine
3'-deoxy-3'-azidothymidine
2',3'-dideoxy-3'-fluoro-5-chlorouridine
2',3'-deoxy-3'-fluorothymidine
2',3'-dideoxy-3'-fluoroadenosine
2',3'-dideoxy-3'-fluoro-2,6-diaminopurine riboside
2',3'-dideoxy-2',3'-didehydrocytidine
3'-deoxy-2',3'didehydrothymidine
3'-deoxy-3'azidothymidine
5-fluorouridine
5-trifluoromethyl-2'-deoxyuridine
6-mercaptopurine-9-β-D-ribofuranoside
2- fluoroadenine-9-β-D-arabinofuranoside
2-chloro-2'-deoxyadenosine
acylclovir and
ganciclovir.

15. The process of claim 1, wherein one of A and B is $C_{10}$–$C_{16}$ alkoxy and the other is $C_{10}$–$C_{16}$ alkylthio.

16. The process of claim 1, wherein $R^2$ is selected from the group consisting of:

3'-deoxy-3'-azidothymidine, 3'-deoxy-3'-fluorothymidine, 5-fluorouridine, 6-mercaptopurine-9-β-D-ribofuranoside, 6-methylmercaptopurine-9-β-D-ribofuranoside, 9-{[(1-hydroxymethyl)ethoxy]-methyl}guanine and 9- (ethoxymethyl)guanine.

\* \* \* \* \*